United States Patent
Chapman (10) Patent No.: US 7,220,961 B2
(45) Date of Patent: May 22, 2007

(54) SYSTEM AND METHOD FOR QUALITY CONTROL IN NUCLEAR IMAGING SYSTEMS

(75) Inventor: James T. Chapman, Glen Ellyn, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 16 days.

(21) Appl. No.: 10/949,056

(22) Filed: Sep. 24, 2004

(65) Prior Publication Data

US 2005/0072914 A1   Apr. 7, 2005

(51) Int. Cl.
*G01D 18/00* (2006.01)

(52) U.S. Cl. .............. 250/252.1; 250/370.09; 378/5

(58) Field of Classification Search .......... 250/252.1, 250/370.09; 378/5
See application file for complete search history.

(56) References Cited

U.S. PATENT DOCUMENTS

| | | | | |
|---|---|---|---|---|
| 5,338,936 | A | * | 8/1994 | Gullberg et al. ....... 250/363.04 |
| 5,358,712 | A | * | 10/1994 | Efange et al. ............. 424/1.65 |
| 5,481,115 | A | * | 1/1996 | Hsieh et al. ............ 250/363.04 |
| 5,990,482 | A | * | 11/1999 | Bertelsen et al. ...... 250/363.04 |
| 6,072,177 | A | * | 6/2000 | McCroskey et al. ..... 250/252.1 |
| 6,140,650 | A | * | 10/2000 | Berlad ................... 250/363.09 |
| 6,694,172 | B1 | * | 2/2004 | Gagnon et al. ............. 600/436 |
| 6,774,358 | B2 | * | 8/2004 | Hamill et al. ............ 250/252.1 |
| 2002/0159561 | A1 | * | 10/2002 | Cederstrom ................... 378/84 |
| 2003/0021375 | A1 | * | 1/2003 | Jones et al. .................... 378/51 |
| 2004/0251419 | A1 | * | 12/2004 | Nelson et al. ......... 250/370.09 |
| 2005/0056788 | A1 | * | 3/2005 | Juni ...................... 250/363.04 |

* cited by examiner

Primary Examiner—Renee Luebke
Assistant Examiner—Mary Zettl (57) ABSTRACT

A method of controlling quality in a nuclear medicine imaging system includes providing an extendable radioactive source in a frame of the nuclear medicine imaging system, providing a detector having a field of view above the source, extending the radioactive source, moving the detector from a first position to a second position, acquiring a plurality of images of the radioactive source with the detector during the movement, summing the plurality of images to form a flood image of the source, and assessing a quality of the detector image using the flood image. An extendable shield having a plurality of windows disposed along a length of the shield may be disposed about a line source so that the windows form an array of point sources when the source and the shield are extended.

42 Claims, 4 Drawing Sheets

SYSTEM AND METHOD FOR QUALITY CONTROL IN NUCLEAR IMAGING SYSTEMS

BACKGROUND OF THE INVENTION

1. Field of Invention

This invention relates to the field of nuclear medicine, and in particular to nuclear medicine imaging systems, and the control of their quality.

2. Description of the Related Art

Nuclear medicine is a unique medical specialty wherein radiation is used to acquire images that show the function and anatomy of organs, bones or tissues of the body. Radiopharmaceuticals are introduced into the body, either by injection or ingestion, and are attracted to specific organs, bones or tissues of interest. Such radiopharmaceuticals produce gamma photon emissions that emanate from the body. One or more detectors are used to detect the emitted gamma photons, and the information collected from the detector(s) is processed to calculate the position of origin of the emitted photon from the source (i.e., the body organ or tissue under study). The accumulation of a large number of emitted gamma positions allows an image of the organ or tissue under study to be displayed.

Proper imaging requires that the camera be calibrated to eliminate or minimize distortions. Such distortions can be caused, for example, by lack of a uniform response to incident radiation over the entire area of the scintillation detector surface, by non-linear responses to incident radiation by different photomultiplier tubes arrayed over the scintillation crystal, and by variations in the energy window defining the range of photon energy levels of a scintillation interaction or "event" that will be accepted as contributing to the image.

Routine quality control of a nuclear imaging system may require the provision of a variety of radioactive sources. The sources are used as baselines to calibrate the camera. The sources may be required to be provided in a variety of configurations, such as a 57Co sheet source and a variety of 99 µTc point and line sources. Furthermore, the point and line sources may need to be prepared on site.

A camera may need to be "peaked" daily before switching to a new radio nuclide to ensure that the energy window is correct. Uniformity may need to be checked daily as well, using a high count flood. In a high count flood, a collimator may be removed and a point source, such as a 57Co disc source or a water-filled phantom may be viewed from a distance of five times the diameter of the detector. A water filled phantom may need to be prepared on site. Camera uniformity may need to be checked weekly.

SUMMARY OF THE INVENTION

In a first aspect of the invention, a method of controlling quality in a nuclear medicine imaging system includes providing an extendable radioactive line source in a frame of the nuclear medicine imaging system, providing a detector having a field of view above the line source, extending the line source, moving the detector from a first position to a second position, acquiring a plurality of images of the line source with the detector, summing the plurality of images to form a flood image of the line source, and assessing a quality of the detector image using the flood image.

In a second aspect of the invention, a method of controlling quality in a nuclear medicine imaging system includes providing an extendable radioactive point source in a frame of the nuclear medicine imaging system, providing a detector having a field of view above the point source, extending the point source in a center of the field of view substantially parallel to the frame, acquiring an image of the point source with the detector, and assessing a quality of the detector image.

In a third aspect of the invention, a nuclear medicine imaging system includes a bed having a frame, a detector having a field of view disposed above the frame, an extendable radioactive line source disposed in the frame, an extendable shield disposed about the line source, the shield having a plurality of windows disposed along a length of the shield, and wherein the windows form an array of point sources when the line source and the shield are extended.

In a fourth aspect of the invention, a system for controlling quality in a nuclear medicine imaging system includes means for providing an extendable radioactive source in a frame of the nuclear medicine imaging system, means for providing a detector having a field of view above the source, means for extending the source, means for moving the detector from a first position to a second position, means for acquiring a plurality of images of the source with the detector, means for summing the plurality of images to form a flood image of the source, and means for assessing a quality of the detector image using the flood image.

In a fifth aspect of the invention, a system for controlling quality in a nuclear medicine imaging system includes means for providing an extendable radioactive point source in a frame of the nuclear medicine imaging system, means for providing a detector having a field of view above the point source, means for extending the point source in a center of the field of view substantially parallel to the frame, means for acquiring an image of the point source with the detector, and means for assessing a quality of the detector image using the image.

In a sixth aspect of the invention, a method of controlling quality in a nuclear medicine imaging system includes acquiring a plurality of images of a radioactive source with a detector during a movement of said detector, summing said plurality of images to form a flood image of said source, and assessing a quality of the detector image using the flood image.

DETAILED DESCRIPTION OF THE PREFERRED EMBODIMENTS

Since quality control of nuclear imaging systems needs to be performed relatively frequently, it may be desirable if the different radioactive sources needed to calibrate the imaging system and to assess performance level characteristics could be combined into a single integrated unit. Furthermore, it may be desirable if the setup and execution of the quality control process could be automated so that it could be conducted overnight, reducing machine downtime.

In particular, it may be desirable if a long lived source of known activity and configuration could be housed in a shielded housing within the frame of a bed. It may further be desirable if an automated means of extending those sources into the field of view of the detector to a known location could be provided. Finally, it may be desirable if those sources could be employed to calibrate the system or assess the quality of the system and detectors.

Furthermore, it may be desirable if radioactive sources could be housed permanently in the bed of the imager. It may also be desirable if a radioactive source could be housed in the bed in such manner so as to relieve support personnel of the requirement of storing permanent sheet sources for floods. It may also be desirable if a radioactive source housed in the bed relieved support personnel of the requirement of preparing liquid point sources for alignment and tuning. Finally, it may be desirable if the process were automated so that a need for human intervention could be reduced or eliminated.

Figure 1:
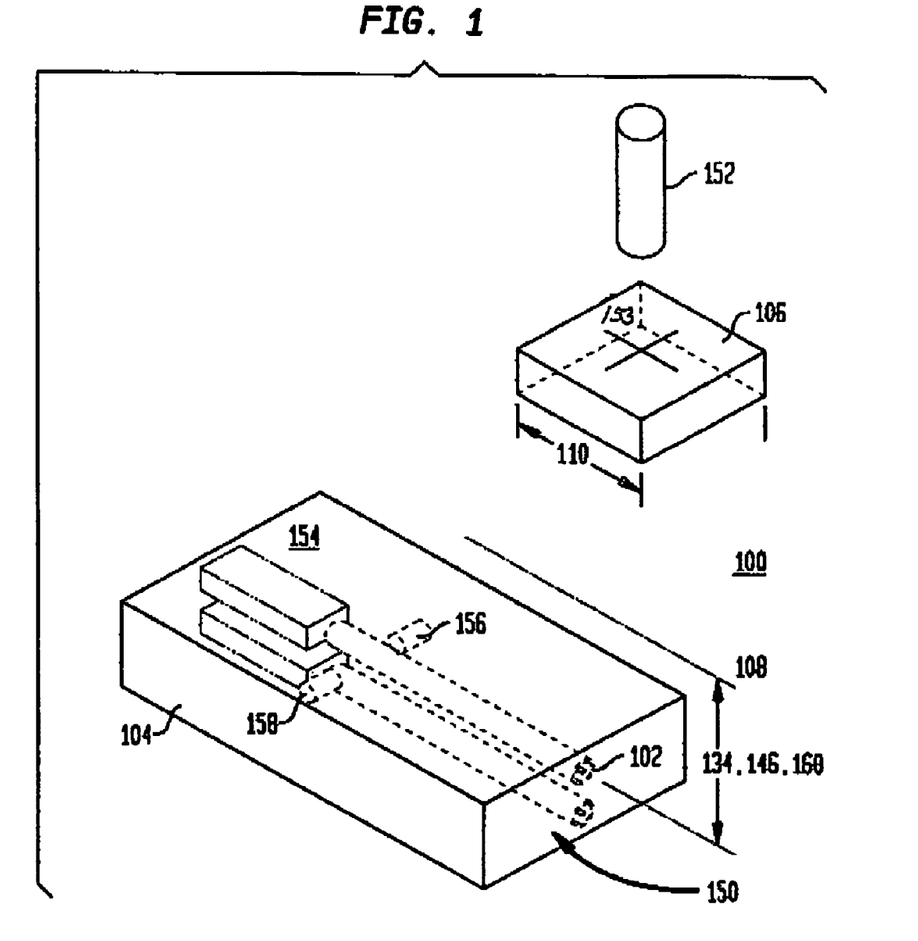
FIG. 1 shows a nuclear imaging system according to a first embodiment of the invention.

A method and apparatus for controlling quality in a nuclear imaging system 100 according to a first embodiment of the invention is shown in FIG. 1. Nuclear imaging system 100 includes a bed 154 which has a frame 104, a detector 106 with an axis of rotation 108 and a field of view 110 disposed above bed 154, and an extendable radioactive source 102 disposed substantially parallel to axis of rotation 108 in frame 104. Frame 104 may be a frame of the bed, of the detector, of a gantry, or a frame in the floor under imaging system 100. Source 102 may be a line source, a point source, or an array of point sources. In one embodiment, source 102 may be a Cobalt-57 (57Co) line source with a length 132 exceeding field of view 110. In various embodiments, source 102 may be Americium-241, Barium-133, or Germanium-68.

In one embodiment, source 102 may be extended substantially parallel to axis of rotation 108 in field of view 110 such that the activity is centered in field of view 110. In various embodiments, an activity of source 102 may be about 5 µCi to 20 µCi, a clinical count rate may be about 5 to 40 kilocounts per sec (kcps), and an activity of source 102 may vary by less than 1% along length 132 of source 102.

Extendable radioactive source 102 may be provided in frame 104 of nuclear imaging system 100. Source 102 may be extended by a motor 156, such as an electric motor. Source 102 may be extended substantially parallel to frame 104. In one embodiment, source 102 may be a 20 µCi to 30 µCi 57Co source. Detector 106 having axis of rotation 108 and field of view 110 may be provided above source 102.

Figure 2:
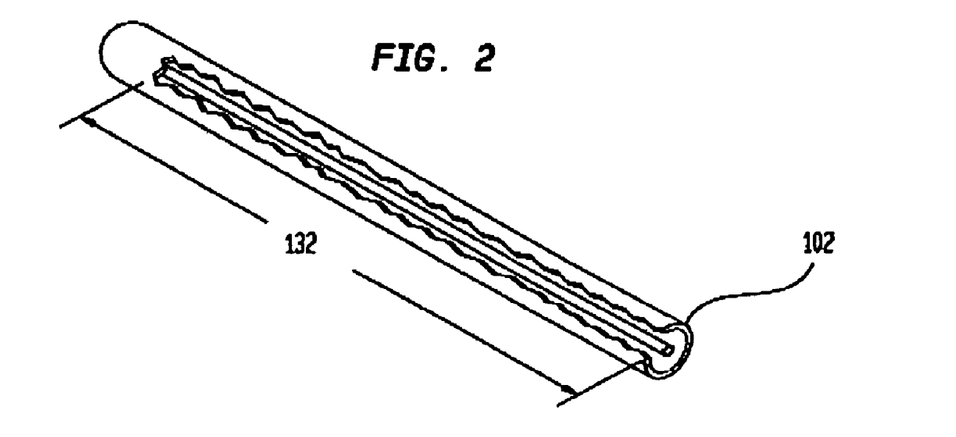
FIG. 2 shows a line source for use with an embodiment of the invention.

As shown in FIG. 2, in one embodiment, length 132 of source 102 may be greater than field of view 110 of the detector 106. In a preferred embodiment, length 132 exceeds field of view 110 by several centimeters (cm). In this embodiment, length 132 may be about 45 cm to 50 cm. In one embodiment as shown in FIG. 1, a vertical distance 134 from source 102 to axis of rotation 108 may be about equal to field of view 110.

Figure 3A:
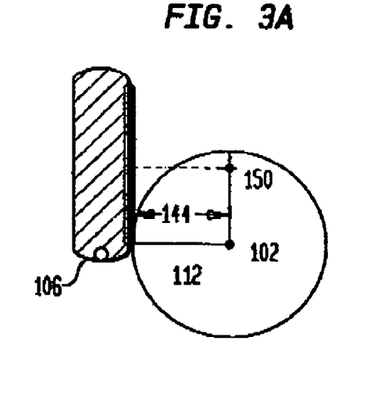
FIGS. 3A–3E show rotation of a detector about a radiation line source for use with an embodiment of the invention.
Figure 3B:
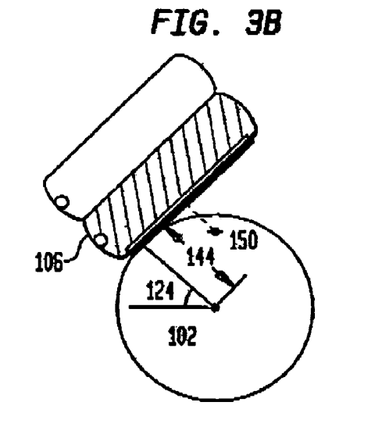
Figure 3C:
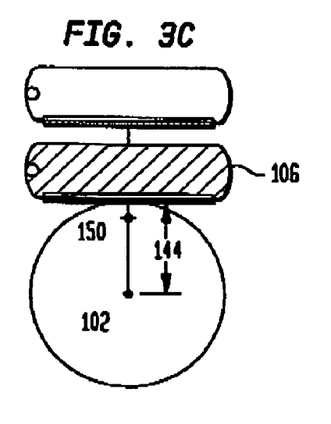
Figure 3D:
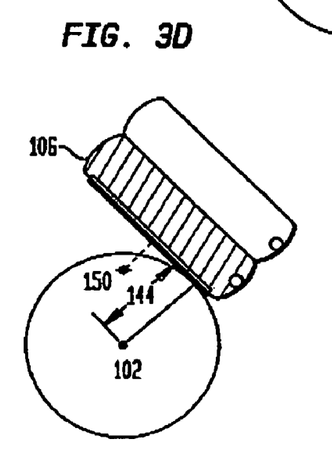
Figure 3E:
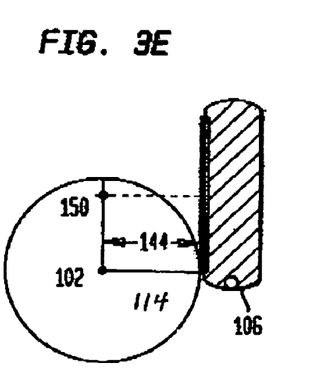

As shown in FIGS. 3A–3E, detector 106 may be moved incrementally from a first position 112 (FIG. 3A) to a second position 114 (FIG. 3E). In one embodiment, detector 106 may be translated incrementally from a first position 112 to a second position 114. In another embodiment, detector 106 may be rotated about axis of rotation 108. In this embodiment, first position 112 may be at substantially −90 E to axis of rotation 108 and second position 114 may be at substantially +90 E to axis of rotation 108. In one embodiment, a substantially predetermined distance 144 may be maintained from detector 106 to source 102 during rotation.

Images 116 of source 102 may be swept across field of view 110 as detector 106 moves from first position 112 to second position 114. Images 116 will thus be projected onto a surface of detector 106 from various angles as detector 106 moves from first position 112 to second position 114. In one embodiment, source 102 may be swept across a transaxial field of view 110 in full or part by moving bed 154 containing source 102 relative to detector 106. In a further embodiment, detector 106 may be oriented at about at ±90E.

In one embodiment, source 102 may be swept across the transaxial field of view 110 of detector 106 by acquiring 180E of a tomographic study in which the sinogram of source 102 sweeps from one side of the transaxial field of view 110 to the other.

Figure 4:
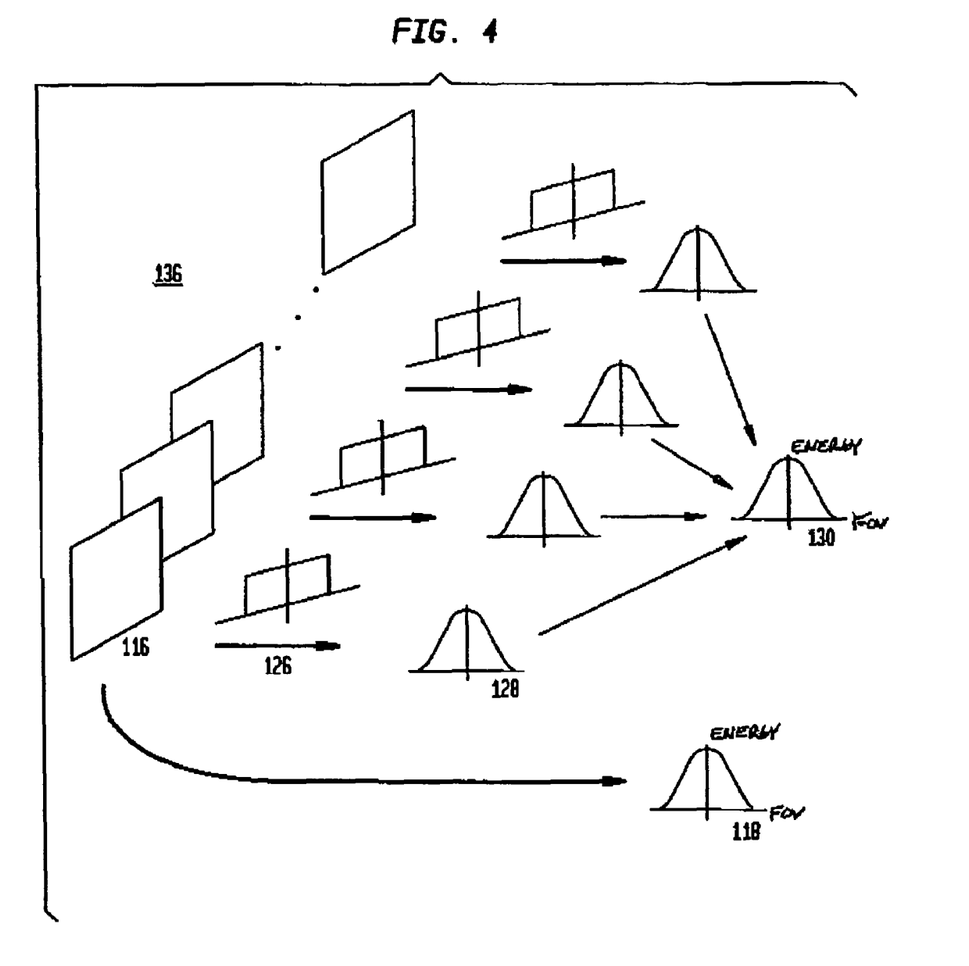
FIG. 4 shows a flood image collection scheme for use with an embodiment of the invention.

As shown in FIG. 4, a plurality of images 116 of source 102 may be acquired with detector 106 during the rotation. Images 116 may be acquired using a step and shoot mode of detector 106. An angular separation 124 between each of images 116 may be spaced such that each projection 160 of each image 116 is displayed substantially evenly across field of view 110.

In one embodiment, source 102 may be assumed to be perfectly straight, uniform, and immobile. Any variation between images 116 may thus be considered to be a result of variations in the intensity of source 102 itself. In one embodiment, predictable non-uniformities among images 116 may be removed by comparing actual source 102 to an image 162 of an ideal line source.

A flood image 118 may be obtained by summing images 116. A uniformity defect due to positional or angular misalignment of source 102 in flood image 118 could be compensated by fitting an ideal response filter 126 to each of images 116, calculating an ideal response 128 for each of images 116, summing ideal responses 128 to form ideal fit data 130, and dividing a sum of images 116 by ideal fit data 130. Ideal response filter 126 may have a Gaussian response.

In one embodiment, images 116 of source 102 may be summed and processed in order to estimate a uniform extrinsic flooding of imaging system 100. In one embodiment, projection 160 may be fit to a idealized model of a perfectly uniform and straight source 102 with a potential offset and slope in projection 160 and a constant system resolution.

In one embodiment, the fits of projection 160 may be further constrained over all projection images 116 to allow only variations consistent with a horizontal and vertical offset of source 102 and a horizontal and vertical deflection of source 102 and the known angular positions of detector 106.

In one embodiment, the fits to projection 160 data may be used to generate ideal image 162 with the same width, intensity, slope, and offset as source 102 but with no variation in intensity of ideal image 162 along the length 132 of source 102 image. In one embodiment, the ideal image 162 may be summed into flood image 118 which may be then used to normalize the summed projection data. This may remove systematic "ripple" nonuniformity due to the summing of a finite number of evenly spaced images 116 of source 102 and gross nonuniformity due to the spatial or angular mis-alignment of source 102 relative to detector 106.

In one embodiment, the summed projection 160 normalized by the flood image 118 may be formatted, saved, processed and displayed in the same fashion as a conventional sheet source flood used to assess the uniformity of a detector response. In one embodiment, multiple images 116 of a source 102 may be acquired in a tomographic study to calibrate or assess the axis of rotation 108 of imaging system 100 as a function of axial position over the field-of-view.

As shown in FIG. 4, a plurality of images 116 of source 402 may be acquired with detector 106 during the rotation. Images 116 may be acquired using a step and shoot mode of detector 106. An angular separation 124 between each of images 116 may be spaced such that each projection of each image 116 is displayed substantially evenly across field of view 110.

In one embodiment, source 102 may be assumed to be perfectly straight, uniform, and immobile. Any variation between images 116 may thus be considered to be a result of variations in the intensity of source 102 itself. In one embodiment, predictable non-uniformities among images 116 may be removed by comparing actual source 102 loan image 126 of an ideal line source.

In one embodiment, image(s) of source 102 may be acquired at known distance from a collimator face and processed to estimate a resolution of imaging system 100.

In one embodiment, images 116 of source 102 maybe summed and processed in order to estimate a uniform extrinsic flooding of imaging system 100. In one embodiment, projection 160 may be fit to a idealized model of a perfectly uniform and straight source 102 with a potential offset and slope in projection 116 and a constant system resolution.

In one embodiment, multiple images 116 of source 102 may be acquired in a tomographic study and reconstructed to estimate the reconstructed system spatial resolution of imaging system 100.

In one embodiment, the fits to projection 160 data may be used to generate ideal image 126 with the same width, intensity, slope, and offset as source 102 but with no variation in intensity of ideal image 126 along the length 132 of source 102 image. In one embodiment the ideal image 126 may be summed into flood image 118 which may be then used to normalize the summed projection data. This may remove systematic "ripple" nonuniformity due to the summing of a finite number of evenly spaced images 116 of source 102 and gross nonuniformity due to the spatial or angular mis-alignment of source 102 relative to detector 106.

In one embodiment, the summed projection 116 normalized by the flood image 118 may be formatted, saved, processed and displayed in the same fashion as a conventional sheet source flood used to assess the uniformity of a detector response. In one embodiment, multiple images 116 of a source 102 may be acquired in a tomographic study to calibrate or assess the axis of rotation 108 of imaging system 100 as a function of axial position over the field-of-view.

In one embodiment, the reconstructed source 102 may be analyzed to estimate a reconstructed resolution in a manner consistent with external standards and methods.

In one embodiment, projection 116 data from the acquisition may be analyzed to generate individual sinograms for each position in the axial field of view 110. In one embodiment, the sinograms may be analyzed to yield the axis of rotation 108 offset of imaging system 100 as a function of the axial location of the sinogram.

In one embodiment, filtered back projection is used for image construction. Back projection alone (without filtering) may result in undesirable image smoothing.

Figure 5:
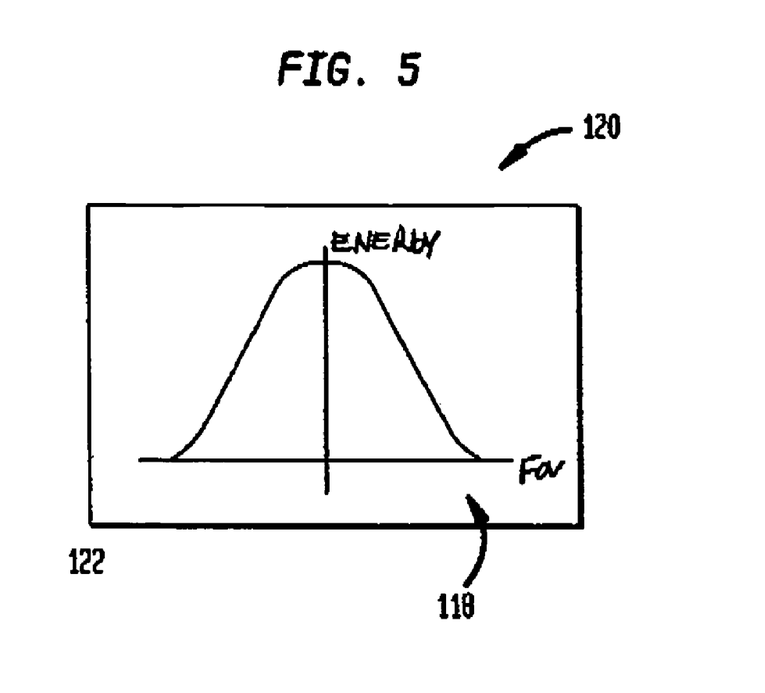
FIG. 5 shows a quality measurement for use with an embodiment of the invention.

Flood image 118 may be used to assess a quality 120 of the detector image 122. In one embodiment, flood image 118 is used to assess a quality distribution, as shown in FIG. 5. In alternative embodiments, quality 120 may be a focus, a peak of irradiation, a uniformity of irradiation, a spatial resolution, a multiple window spatial registration, or a position of detector 106 relative to source 102.

Spatial resolution is a measure of an imager's capability to reproduce fine detail. Spatial resolution may be expressed as a full width at half maximum (FWHM). The larger the FWHM value, in general, the greater the image blur. Smaller FWHM values indicate therefore better detector resolution. In one embodiment, a standard deviation 136 ($\sigma$) of images 116 may be measured, and axis of rotation 108 may be adjusted to minimize standard deviation 136.

Figure 6:
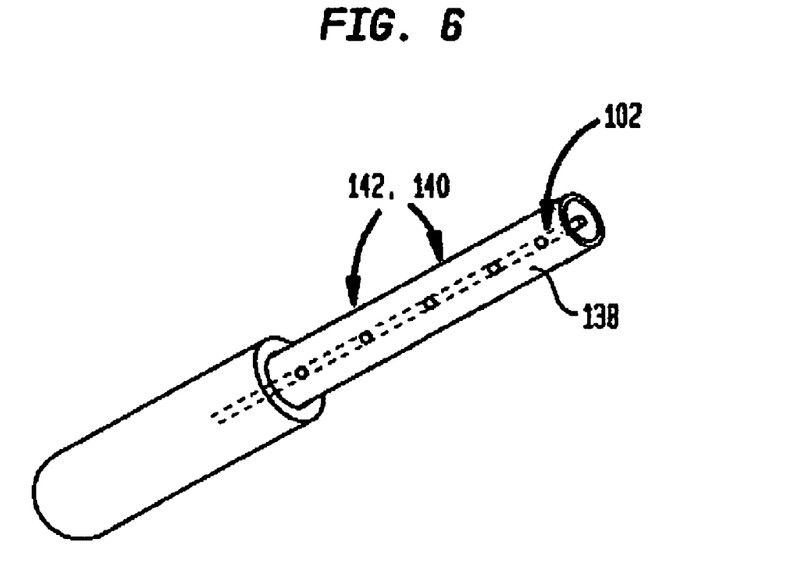
FIG. 6 shows a line source for use with an embodiment of the invention.

In another embodiment, as shown in FIG. 6, an extendable shield 138 may be disposed about source 102. Shield 138 may have a plurality of windows 142 disposed along a length of shield 138. Windows 142 may form an array of point sources 140 when source 102 and shield 138 are extended. Shield 138 may be comprised of lead or tungsten. In alternative embodiments, windows 142 are formed of a low-Z material such as plastic, Lucite, concrete, or aluminum.

In one embodiment, a vertical distance 134 from source 102 to axis of rotation 108 may be about equal to field of view 110. In one embodiment, source 102 may be offset vertically from axis of rotation 108 a distance 146 of substantially one half of field of view 110. In another embodiment, source 102 may be offset vertically from axis of rotation 108 a distance 160 of substantially one fourth field of view 110, and a multiple head registration calibration may be performed.

In one embodiment, source 102 includes an array 140 of point sources 150. Array 140 may be driven out automatically parallel to frame 104 into field of view 110. A strength of source 102 may be chosen to provide count rates between 1 kcps and 40 kcps.

In one embodiment, array 140 may be created by shielding a source 102 employed for other calibrations and measurements with a shield 138. Shield 138 may be driven out automatically and independently of source 102. Shield 138 may enclose the extended source 102 except at regularly spaced location in shield 138. At these locations may be windows 142 filled with low-Z material to convert source 102 into an array 140 of point sources 150 at known axial locations in detector 106 field of view 110.

In one embodiment, array 140 of point sources 150 may be imaged in a tomographic study and the images 116 of point sources 150 may be analyzed to calibrate or verify imaging system 100's axis of rotation 108 at each of the axial locations of point sources 150.

In one embodiment, bed 154 may be driven up down such that array 140 of point sources 150 may be offset vertically from the axis of rotation 108 of imaging system 100 by approximately one-fourth the dimension of the field of view 110. In one embodiment, source 102 may be imaged as a conventional 360E tomographic orbit with sufficient views to characterize the sinogram of source 102 over an orbit of detector 106.

In one embodiment, projection 160 data from the acquisition may be analyzed to generate individual sinograms for each position in field of view 110. In one embodiment, the sinograms may be analyzed to yield the axis of rotation 108 offset of imaging system 100 as a function of the axial location of the sinogram. In one embodiment, the array 140 of point sources 150 may be imaged by multiple detectors 106 in a tomographic study and images 116 of point source 150 may be analyzed to register the axial location of detectors 106 to one another.

In one embodiment, bed 154 may be driven up and down such that array 140 of point sources 150 may be offset vertically from the axis of rotation 108 of imaging system 100 by approximately one-fourth the dimension of the field of view 110. In one embodiment, source 102 may be imaged as a conventional 360E tomographic orbit with sufficient views to characterize the linograms of source 102 over an orbit of detector 106.

In one embodiment, projection 160 data from the acquisition may be analyzed to generate individual linograms for each position and each detector 106 in the axial field of view 110.

In one embodiment, the linograms may be analyzed to yield an axial shift of one detector 106 relative to another detector 106 of imaging system 100 as a function of the axial location of the linograms.

In one embodiment, array 140 of point sources 150 may be imaged to assess the planar resolution of imaging system 100.

In one embodiment, detector 106 may be rotated to 0 E and bed 154 and radial height may be adjusted to achieve a known distance between the source array 140 and detector 106.

In one embodiment, image 116 of array 140 of point sources 150 may be analyzed to yield a planar resolution measurement consistent in a manner consistent with external standards and methods.

In one embodiment, projection 116 data from the acquisition may be analyzed to generate individual sinograms for each position in field of view 110. In one embodiment, the sinograms maybe analyzed to yield the axis of rotation 108 offset of imaging system 100 as a function of the axial location of the sinogram. In one embodiment, the array 140 of point sources 150 may be imaged by multiple detectors 106 in a tomographic study and images 116 of point soiree 150 may be analyzed to register the axial location of detectors 106 to one another.

In one embodiment, detectors 106 may be brought in to a known radius and array 140 of point sources 150 may be placed at a known offset from the central field-of-view.

In one embodiment, projection 116 data from the acquisition may be analyzed to generate individual linograms for each position and each detector 106 in the axial field of view 110.

In one embodiment, the reconstructed point source array 140 may be analyzed to yield an estimate of reconstructed resolution in a manner consistent with external standards and methods.

In one embodiment, array 140 of point sources 150 may be imaged in a tomographic study and the images 116 may be analyzed to diagnose mechanical mis-alignments or offsets of imaging system 100.

In one embodiment, array 140 of point sources 150 may be acquired in a sequence of standard tomographic acquisitions with known motions of imaging system 100 axis between each acquisition.

In one embodiment, the location of the reconstructed points may be compared to their expected positions given the motions of imaging systems 100 axis and a trueness of drive motion may be assessed.

In one embodiment, the individual linograms and sinograms of point sources 150 may be analyzed for deviations and offset consistent with system mis-alignment or deflection during tomographic acquisition.

In one embodiment, point source 150 may be a Co-57 point source. Point source 150 may be extended to a position centered both transaxially and axially in detector 106's field of view 110. Activity of point source (10–40 μCi) may be chosen so as to produce clinical count rates (5–40 kcps) when imaged by detector 106 with no collimator in place.

In one embodiment, point source 150 illuminates the stationary detector 106 at approximately one-field of view 110 and may be used to tune an individual photo-multiplier tube (PMT) in imaging system 100.

In one embodiment, point source 150 illuminates the stationary detector 106 at approximately one-field of view 110 and may be used to generate an intrinsic calibration map for imaging system 100.

In one embodiment, point source 150 illuminates the stationary detector 106 at approximately one-field of view 110 and may be used to assess the intrinsic uniformity of imaging system 100.

In one embodiment, point source 150 illuminates the stationary detector 106 at approximately one-field of view 110 and may be used to estimate the energy resolution of imaging system 100.

In one embodiment, point source 150 illuminates the stationary detector 106 at approximately one-field of view 110 and may be used to calibrate the energy correction map for imaging system 100.

In one embodiment, point source 150 illuminates the stationary detector 106 at approximately one-field of view 110 and may be used to adjust the linearity correction calibration of imaging system 100.

In one embodiment, as shown in FIG. 1, an extendable radioactive point source 150 may be disposed substantially parallel to axis of rotation 108 below source 102 in frame 104 of nuclear imaging system 100. Point source 150 may be a 30 μCi $^{57}$ Co point source. Point source 150 may be extended by a motor 158, such as an electric motor. Point source 150 may be extended in a center 153 of field of view 110 substantially parallel to frame 104.

Image 116 of point source 150 may be acquired with detector 106, and a quality 120 of detector 106 image may be assessed using image 116. In alternative embodiments, quality 120 may represent a focus, a peak of irradiation, a uniformity of irradiation, a spatial resolution, a multiple window spatial registration, or a position of detector 106 relative to point source 150.

In one embodiment, a collimator 152 of nuclear imaging system 100 may be removed and an intrinsic flood acquisition may be performed, detector 106 may be tuned, or detector 106 may be peaked. Collimator 152 may be a parallel hole, converging, diverging, or pinhole collimator.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. A method of controlling quality in a nuclear medicine imaging system comprising: providing an extendable radioactive source in a frame of said nuclear medicine imaging system; providing a detector having a field of view above said source; extending said source; moving said detector from a first position to a second position; acquiring a plurality of images of said source with said detector during said movement; summing said plurality of images to form a flood image of said source; assessing a quality of the detector image using the flood image; and calibrating said nuclear medicine imaging system based on said assessment.

2. The method of controlling quality of claim 1, wherein said source is selected from the group consisting of: a line source, a point source, and an array of point sources.

3. The method of controlling quality of claim 1, wherein said movement comprises rotating said detector about an axis of rotation of said detector from said first position to said second position.

4. The method of controlling quality of claim 3, comprising further maintaining a substantially predetermined distance from said detector to said source during said rotation.

5. The method of controlling quality of claim 3, comprising further spacing an angular separation between each of said plurality of images such that a projection of each said image is displayed substantially evenly across said field of view.

6. The method of controlling quality of claim 3, wherein forming said flood images comprises further: fitting an ideal response filter to each of said plurality of images; calculating an ideal response for each of said images; summing said ideal responses to form an ideal fit data; and dividing said flood image by said ideal fit data.

7. The method of controlling quality of claim 3, wherein said first position is at substantially −90 E to said axis of rotation and said second position is at substantially +90 E to said axis of rotation.

8. The method of controlling quality of claim 3, wherein said images are acquired using a step and shoot mode of said detector.

9. The method of controlling quality of claim 3, wherein a vertical distance from said source to said axis of rotation is about equal to said field of view.

10. The method of controlling quality of claim 3, comprising further: offsetting said source vertically from said axis of rotation a distance of substantially one fourth said field of view; and performing a multiple head registration calibration.

11. The method of controlling quality of claim 1, wherein said source is a line source having a length greater than said field of view.

12. The method of controlling quality of claim 1, comprising further measuring a standard deviation of said plurality of images; and adjusting said axis of rotation to minimize said standard deviation.

13. The method of controlling quality of claim 1, wherein extending said source comprises further: providing an extendable shield about said source, said shield having a plurality of windows disposed along a length of said shield; and extending said shield to form an array of point sources.

14. The method of controlling quality of claim 13, wherein said shield is comprised of lead or tungsten.

15. The method of controlling quality of claim 14, wherein said plurality of windows are formed of a low-Z material.

16. The method of controlling quality of claim 15, wherein said low-Z material is selected from the group consisting of: plastic, Lucite, concrete, and aluminum.

17. The method of controlling quality of claim 1, wherein said quality is selected from the group consisting of: a focus, a peak of irradiation, a uniformity of irradiation, a spatial resolution, a multiple window spatial registration, and a position of said detector relative to said source.

18. A method of controlling quality in a nuclear medicine imaging system comprising: providing an extendable radioactive point source in a frame of said nuclear medicine imaging system; providing a detector having a field of view above said point source; extending said point source in a center of said field of view; acquiring an image of said point source with said detector; assessing a quality of the detector using the image; and calibrating said nuclear medicine imaging system based on said assessment.

19. The method of controlling quality of claim 18, comprising further: removing a collimator of said nuclear imaging system; and performing an intrinsic flood acquisition.

20. The method of controlling quality of claim 18, comprising further: removing a collimator of said nuclear imaging system; and tuning said detector.

21. The method of controlling quality of claim 18, comprising further: removing a collimator of said nuclear imaging system; and peaking said detector.

22. The method of controlling quality of claim 18, wherein said quality is selected from the group consisting of: a focus, a peak of irradiation, a uniformity of irradiation, a spatial resolution, a multiple window spatial registration, and a position of said detector relative to said point source.

23. The method of controlling quality of claim 18, comprising further measuring a standard deviation of said plurality of images; and adjusting an axis of rotation of said detector to minimize said standard deviation.

24. A nuclear medicine imaging system comprising: a frame; a bed disposed on said frame; a detector having a field of view disposed above said bed; and an extendable radioactive source disposed in said frame and substantially parallel to an axis of rotation of said detector.

25. The nuclear medicine imaging system of claim 24, wherein a length of said source is greater than said field of view.

26. The nuclear medicine imaging system of claim 24, comprising further an extendable shield disposed about said source, said shield having a plurality of windows disposed along a length of said shield, and wherein said windows form an array of point sources when said source and said shield are extended.

27. The nuclear medicine imaging system of claim 26, wherein said plurality of windows are formed of a low-Z material.

28. The nuclear medicine imaging system of claim 27, wherein said low-Z material is selected from the group consisting of: plastic, Lucite, concrete, and aluminum.

29. The nuclear medicine imaging system of claim 24, comprising further an extendable radioactive point source disposed below said source in said frame.

30. A system for controlling quality in a nuclear medicine imaging system comprising: means for providing an extendable radioactive source in a frame of said nuclear medicine imaging system; means for providing a detector having a field of view above said source; means for extending said source substantially parallel to said frame; means for moving said detector from a first position to a second position; means for acquiring a plurality of images of said source with said detector during said movement; means for summing said plurality of images to form a flood image of said source; means for assessing a quality of the detector image using the flood image; and means for calibrating said nuclear imaging system based on said assessment.

31. The method of controlling quality of claim 30, wherein said means for moving said detector comprises means for rotating said detector about an axis of rotation of said detector from said first position to said second position.

32. The system for controlling quality of claim 31, comprising further: means for offsetting said source vertically from an axis of rotation of said detector a distance of substantially one fourth said field of view; and means for performing a multiple head registration calibration.

33. The system for controlling quality of claim 30, comprising further means for maintaining a substantially predetermined distance from said detector to said source during said movement.

34. The system for controlling quality of claim 30, comprising further means for spacing an angular separation between each of said plurality of images such that a projection of each said image is displayed substantially evenly across said field of view.

35. The system for controlling quality of claim 30, wherein said means for forming said flood images comprises further: means for fitting an ideal response filter to each of said plurality of images; means for calculating an ideal response for each of said images; means for summing said ideal responses to form an ideal fit data; and means for dividing said flood image by said ideal fit data.

36. The system for controlling quality of claim 30, comprising further:
means for measuring a standard deviation of said plurality of images; and means for adjusting an axis of rotation of said detector to minimize said standard deviation.

37. The system for controlling quality of claim 30, wherein said means for extending said source comprises further: means for providing an extendable shield about said source, said shield having a plurality of windows disposed along a length of said shield; and means for extending said shield to form an array of point sources.

38. A system for controlling quality in a nuclear medicine imaging system comprising: means for providing an extendable radioactive point source in a frame of said nuclear medicine imaging system; means for providing a detector having a field of view above said point source; means for extending said point source in a center of said field of view; means for acquiring an image of said point source with said detector; means for assessing a quality of the detector image using the flood image; and means for calibrating said nuclear imaging system based on said assessment.

39. The system for controlling quality of claim 38, comprising further: means for removing a collimator of said nuclear imaging system; and means for performing an intrinsic flood acquisition.

40. The system for controlling quality of claim 38, comprising further: means for removing a collimator of said nuclear imaging system; and means for tuning said detector.

41. The system for controlling quality of claim 38, comprising further: means for removing a collimator of said nuclear imaging system; and means for peaking said detector.

42. A method of controlling quality in a nuclear medicine imaging system comprising: acquiring a plurality of images of a radioactive source with a detector during a movement of said detector; summing said plurality of images to form a flood image of said source; assessing a quality of the detector image using the flood image; and calibrating said nuclear imaging system based on said assessment.

* * * * *